US00PP23405P2

(12) United States Plant Patent
van Kleinwee

(10) Patent No.: US PP23,405 P2
(45) Date of Patent: Feb. 19, 2013

(54) ***OSTEOSPERMUM* PLANT NAMED 'OSTZ0001'**

(50) Latin Name: *Osteospermum ecklonis*
Varietal Denomination: OSTZ0001

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,887

(22) Filed: Oct. 31, 2011

(51) Int. Cl.
*A01H 5/00* (2006.01)

(52) U.S. Cl. ..... Plt./360

(58) Field of Classification Search ..... Plt./360
See application file for complete search history.

*Primary Examiner* — Kent L Bell
(74) *Attorney, Agent, or Firm* — Joshua L. Price

(57) ABSTRACT

A new *Osteospermum* plant named 'OSTZ0001' particularly distinguished by the light yellow-orange to red-orange bicolored inflorescences held well above the foliage on relatively long peduncles, medium-deep green foliage, semi-upright plant habit with relatively vigorous growth habit.

1 Drawing Sheet

Latin name of the genus and species of the plant claimed: *Osteospermum ecklonis*.

Varietal denomination: 'OSTZ0001'.

BACKGROUND OF THE NEW PLANT

The present invention comprises a *Osteospermum*, botanically known as *Osteospermum ecklonis* and hereinafter referred to by the variety name 'OSTZ0001'.

'OSTZ0001' is a product of a planned breeding program. The new cultivar has light yellow-orange to red-orange bicolored inflorescences held well above the foliage on relatively long peduncles, medium-deep green foliage, semi-upright plant habit with relatively vigorous growth habit.

'OSTZ0001' originated from an open pollination occurring in the summer of 2006 in a controlled environment in Enkhuizen, Netherlands. The female parent was the unpatented, proprietary plant designated '60145', with bronze flower color, and more mounding and less upright plant habit, with more branching.

The male parent of 'OSTZ0001' is not known.

The resulting seeds were sown in Enkhuizen, Netherlands in March 2007. 'OSTZ0001' was selected as one flowering plant within the progeny of the stated cross in August 2007.

The first act of asexual reproduction of 'OSTZ0001' was accomplished when vegetative cuttings were propagated from the initial selection in October 2007 in a controlled environment in Enkhuizen, Netherlands.

BRIEF SUMMARY OF INVENTION

Horticultural examination of plants grown from cuttings of the plant initiated in the spring of 2008 in Enkhuizen and Andijk, Netherlands, and continuing thereafter, has demonstrated that the combination of characteristics as herein disclosed for 'OSTZ0001' are firmly fixed and are retained through successive generations of asexual reproduction.

'OSTZ0001' has not been observed under all possible environmental conditions. The phenotype may vary significantly with variations in environment such as temperature, light intensity and day length.

Plant Breeder's Rights for this cultivar have been applied in Canada on Dec. 24, 2010, #10-7141 and at the Community Plant Variety Office on Oct. 15, 2010, #2010/2178. 'OSTZ0001' has not been made publicly available more than one year prior to the filing of this application.

The following traits have been repeatedly observed and are determined to be basic characteristics of the new variety. The combination of these characteristics distinguishes this *Osteospermum* as a new and distinct variety.

BRIEF DESCRIPTION OF THE PHOTOGRAPHS

Figure 1:
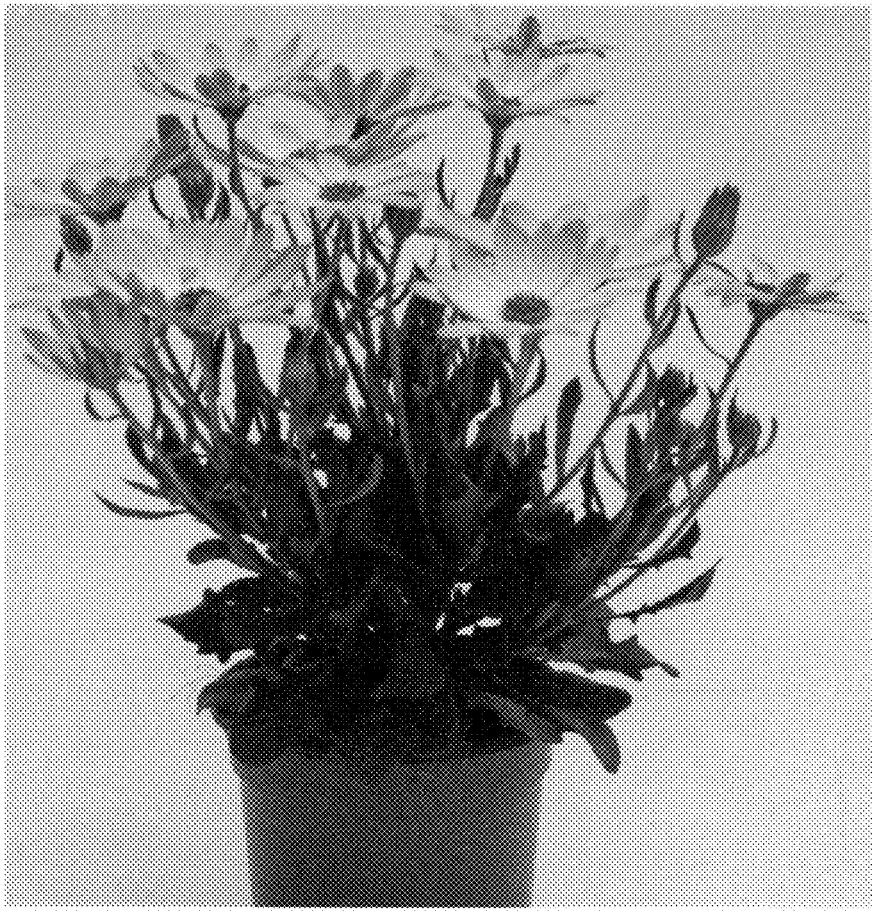
Figure 2:
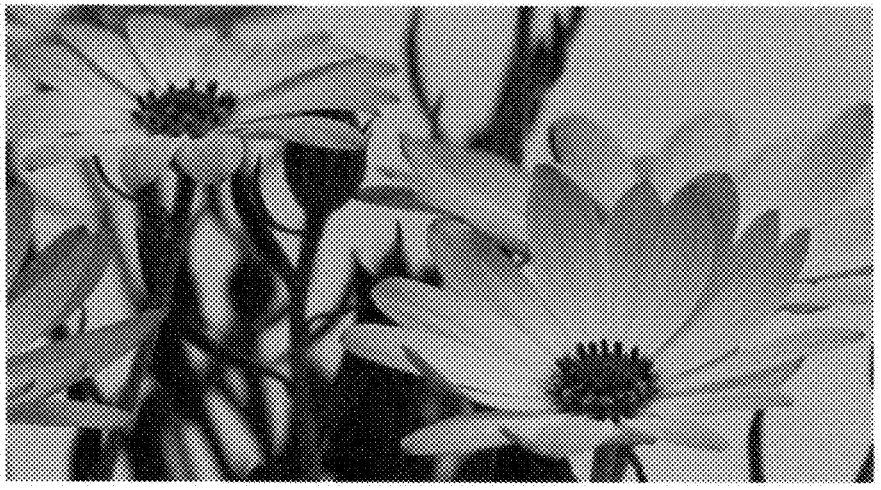

The accompanying photographic drawing shows typical flower and foliage characteristics of 'OSTZ0001' with colors being as true as possible with an illustration of this type. The photographic drawing shows in FIG. 1. a flowering plant of the new variety, and in FIG. 2. a close-up of the inflorescences.

DETAILED BOTANICAL DESCRIPTION

The aforementioned photographs were taken in mid June 2011 from plants grown in a greenhouse trial in Enkhuizen, Netherlands. These plants were growing in 10.5 cm pots and were approximately 3 months of age.

The plant descriptions and measurements were taken in Andijk, Netherlands in mid May 2011 using 12 week old greenhouse grown plants. Plants were grown in 10.5 cm pots at a minimum temperature of 16-18° C. in the greenhouse.

Color references are made to The Royal Horticultural Society Colour Chart (R.H.S.) 2001.

DIFFERENCES BETWEEN THE NEW VARIETY 'OSTZ0001' AND A SIMILAR VARIETY

| | 'OSTZ0001' | 'Tra Terra' (U.S. Plant Pat. No. 22,419) |
|---|---|---|
| Ray floret color: | More of a greyed-red overlay in longitudinal patterns; with a distinct | More yellow-orange or orange-red colors in horizontal block patterns |

-continued

| DIFFERENCES BETWEEN THE NEW VARIETY 'OSTZ0001' AND A SIMILAR VARIETY | | |
|---|---|---|
| | 'OSTZ0001' | 'Tra Terra' (U.S. Plant Pat. No. 22,419) |
| | greyed-purple blotch basally | from the disc to petal apex |
| Foliage habit: | Minimal quantity of leaves per plant, mostly on the lower portion of stems | Appears more 'leafy', with more foliage per plant |
| Foliage color: | Little more deeper green | Little lighter green |
| Plant habit: | Shorter | Taller |

Plant:

*Plant habit*.—Initially appears more semi-upright and later becoming more spreading, moderately tight canopy of medium branching, with the inflorescences held well above the foliage on relatively long and strong peduncles.

*Plant height* (*without inflorescences*).—10.0-15.0 cm.

*Plant height* (*inflorescence incl.*).—20.0-23.0 cm.

*Plant width*.—25.0-28.0 cm.

Roots:

*Number of days to initiate and develop roots*.—24-27 days at about 22 degrees C.

*Type*.—Fine, fibrous, free branching.

*Color*.—RHS N155B but whiter.

Foliage:

*Arrangement*.—Alternate, simple leaves; minimal quantity of foliage per stem than normal.

*Immature, leaf color, upper surface*.—RHS 143A.

*Lower surface*.—RHS 143B.

*Mature, leaf color, upper surface*.—RHS 137A, sometimes a little darker.

*Lower surface*.—RHS 138A.

*Length*.—5.5-6.0 cm.

*Width*.—2.9-4.0 cm.

*Shape*.—Oblanceolate.

*Base shape*.—Attenuate.

*Apex shape*.—Obtuse or rounded.

*Margin*.—Dentate.

*Texture, upper surface*.—Slightly glossy, appears glabrous.

*Lower surface*.—Very short, fine hair mostly along the veins.

*Color of veins, upper surface*.—Indistinct.

*Color of veins, lower surface*.—RHS145A for the midrib, RHS144A or 144B for the finer veins.

*Petiole color*.—Upper surface RHS 144B, lower surface RHS 145A.

*Petiole length*.—1.0-1.5 cm.

*Diameter*.—0.4 cm.

*Texture*.—Fine hair along the edges.

Stem:

*Quantity of main branches per plant*.—About 6-10, each developing 3-5 stems with terminal inflorescences.

*Color of stem*.—RHS 143C.

*Length of stem*.—About 17.0-21.0 cm.

*Diameter*.—0.3 cm at midpoint.

*Length of internodes*.—1.0-3.0 cm.

*Texture*.—Sparse short hair.

Peduncle:

*Color of peduncle*.—RHS 143B.

*Length of peduncle*.—About 3-5 cm.

*Peduncle diameter*.—0.2-0.25 cm.

*Texture*.—Covered with short, stiff hair.

Inflorescence:

*Type*.—Capitulum (compositae-type), single inflorescences, borne terminally, with 1-2 whorls of ray florets.

*Quantity of inflorescences*.—15-20 open flowers, plus several more buds.

*Lastingness of individual blooms on the plant*.—About one week, depending on temperature.

*Fragrance*.—None.

Bud (just before opening):

*Color*.—About RHS 179A.

*Length*.—1.7 cm.

*Width*.—0.8 cm.

*Shape*.—Elliptical.

Immature inflorescence:

*Diameter*.—About 3.0-3.5 cm, with the ray florets slanting upward.

*Color of ray florets*.—RHS 18A at basal portion, RHS 26A or RHS 168C at upper portion.

*General color of 'disc' with disc florets still closed*.—About RHS N187B.

Mature inflorescence:

*Shape*.—Flat; rays are nearly horizontally directed when mature.

*Diameter of the whole inflorescence*.—6.7-7.5 cm.

*Diameter of 'disc'*.—1.3 cm.

*Diameter of receptacle*.—0.8 cm at base of florets.

Ray florets:

*Average quantity of ray florets*.—16-19.

*Color of florets, upper surface*.—Mostly RHS 19D with RHS N155C to RHS N155D at the very base, RHS 31C to RHS 31D towards the apex and a spot of RHS 31A at the apex.

*Color of lower surface*.—Closest to RHS 167C at the margins with RHS 166C down the middle.

*Length*.—3.0-3.4 cm.

*Width*.—0.8-0.9 cm.

*Shape*.—Ensiform or oblanceolate.

*Apex shape*.—Rounded to sometimes very slightly praemorse.

*Margin*.—Entire.

*Texture, upper surface*.—Glabrous; with hair (pappus) at base.

*Texture, lower surface*.—Mostly smooth and glabrous, slightly protruding veins.

Disc florets:

*Average quantity of disc florets*.—About 45.

*Color of young* (*just before opening*) *floret at apex*.—RHS N187C.

*Color of open floret*.—RHS N155B with RHS 75B at apex.

*Length of floret*.—0.7-0.8 cm.

*Width at apex*.—0.2 cm.

*Apex shape*.—Acute, 5 pointed.

Phyllaries:

*Quantity of phyllaries*.—19-21.

*Color, outer surface*.—RHS 137B.

*Color, inner surface*.—RHS 137D.

*Length*.—1.3 cm.

*Width*.—0.2 cm.

*Shape*.—Ligulate.

*Apex shape*.—Acute.

*Base*.—Sessile, fused with receptacle.

*Margins*.—Entire.

*Texture outer surface*.—Rough with very short hair.

*Texture inner surface*.—Glossy and glabrous.

Reproductive organs:

*Gynoecium*.—Pistil: One. Length: 0.7 cm. Style color: RHS 69D basal part, with about RHS 70C under the stigma. Style length: 0.3-0.4 cm. Stigma color: RHS 60D. Stigma shape: Bi-lobed.

*Androecium*.—Stamina: Present in disc florets only, 5 per floret, fused and forming a tube. Color of filaments: RHS N155B. Length filaments: 0.2 cm. Anther color: N187A at tip, fading towards base. Color of pollen: RHS 17B. Pollen amount: Plenty (normal amount). Fertility/seed set: Has not been observed on this hybrid. Disease/pest resistance: Has not been observed on this hybrid.

What is claimed is:

1. A new and distinct variety of *Osteospermum* plant named 'OSTZ0001' substantially as illustrated and described herein.

* * * * *